United States Patent
Stern

(10) Patent No.: US 7,247,762 B2
(45) Date of Patent: Jul. 24, 2007

(54) PROCESS FOR XYLENE ISOMERIZATION AND ETHYLBENZENE CONVERSION

(75) Inventor: David L. Stern, Annandale, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 492 days.

(21) Appl. No.: 10/661,985

(22) Filed: Sep. 12, 2003

(65) Prior Publication Data

US 2005/0059847 A1    Mar. 17, 2005

(51) Int. Cl.
  *C07C 5/29* (2006.01)
(52) U.S. Cl. .................................. 585/481; 585/482
(58) Field of Classification Search ............... 585/481, 585/482
  See application file for complete search history.

(56) References Cited

U.S. PATENT DOCUMENTS

| | | | |
|---|---|---|---|
| 3,140,249 A | 7/1964 | Plank et al. | |
| 3,140,251 A | 7/1964 | Plank et al. | |
| 3,140,253 A | 7/1964 | Plank et al. | |
| 3,354,078 A | 11/1967 | Maile et al. | |
| 4,117,026 A | 9/1978 | Haag et al. | |
| 4,159,282 A | 6/1979 | Olsen et al. | |
| 4,163,028 A | 7/1979 | Tabak et al. | |
| 4,312,790 A | 1/1982 | Butter et al. | |
| 4,375,458 A | 3/1983 | Dwyer et al. | |
| RE31,782 E | 12/1984 | Olsen et al. | |
| 4,899,011 A | 2/1990 | Chu et al. | 585/481 |
| 5,028,573 A | 7/1991 | Brown et al. | |
| 5,516,956 A | 5/1996 | Abichandani et al. | 585/481 |
| 5,689,027 A | 11/1997 | Abichandandi et al. | |
| 5,705,726 A | 1/1998 | Abichandandi et al. | |
| 6,008,425 A | 12/1999 | Mohr et al. | 585/481 |
| 6,576,581 B1 | 6/2003 | Sharma et al. | 502/66 |

FOREIGN PATENT DOCUMENTS

| | | |
|---|---|---|
| EP | 0 434 347 A1 | 6/1991 |
| WO | WO02/088056 A1 | 11/2002 |

OTHER PUBLICATIONS

"Journal of Catalysis", vol. 4, p. 527 (1965).
"Journal of Catalysis", vol. 6, p. 278 (1966).
"Journal of Catalysis", vol. 61, p. 395 (1980).

*Primary Examiner*—Thuan D Dang

(57) ABSTRACT

A process for the isomerization of xylenes and the conversion of ethylbenzene to benzene and ethane using a catalyst system comprising two catalysts. The first catalyst is unselectivated and comprises: (a) an intermediate pore size zeolite, e.g., ZSM-5; (b) at least one hydrogenation component to deethylate ethylbenzene, e.g. Group VIII and/or Group VIIIB metal; and (c) an amorphous binder, said first catalyst requiring at least 50 minutes to sorb 30% of the equilibrium capacity of ortho-xylene at 120° C. and at an ortho-xylene partial pressure of 4.5±0.8 mm of mercury. The second catalyst comprises an intermediate pore size zeolite, e.g., ZSM-5, and requires less than 50 minutes to sorb 30% of the equilibrium capacity of ortho-xylene at 120° C. and at an ortho-xylene partial pressure of 4.5±0.8 mm of mercury. The amount of first catalyst present in the catalyst system is a volume greater than 55 percent based on the sum of the volumes of the first catalyst and second catalyst.

36 Claims, No Drawings

PROCESS FOR XYLENE ISOMERIZATION AND ETHYLBENZENE CONVERSION

FIELD OF THE INVENTION

This invention relates to a process for the isomerization of xylenes and the conversion of ethylbenzene to benzene and ethane using a two catalyst system.

BACKGROUND OF THE INVENTION

Para-xylene is a valuable chemical feedstock, which may be derived from mixtures of $C_8$ aromatics separated from such raw materials as petroleum naphthas, particularly reformates, usually by selective solvent extraction. The $C_8$ aromatic fractions from these sources vary quite widely in composition, but will usually be in the range of 10 to 32 wt. % ethylbenzene with the balance xylenes, being divided approximately 50 wt. % meta-xylene and 25 wt. % each of para-xylene and ortho-xylene.

Individual isomer products may be separated from the naturally occurring mixtures by appropriate physical methods. Ethylbenzene may be separated by fractional distillation, although this is a costly operation. Ortho-xylene may be separated by fractional distillation, and is so produced commercially. Para-xylene may be separated from the mixed isomers by fractional crystallization, selective adsorption, or membrane separation.

As commercial use of para-xylene has increased, combining physical separation with chemical isomerization of the other xylene isomers to increase the yield of the desired para-isomer has become increasingly important. However, since the boiling point of ethylbenzene is very close to those of para-xylene and meta-xylene, complete removal of ethylbenzene from the $C_8$ aromatic feed by distillation is impractical. Hence an important feature of any commercial xylene isomerization process is the ability to convert ethylbenzene in the feed while simultaneously minimizing any conversion of xylenes to other compounds.

Various methods for isomerizing xylenes and converting ethylbenzene have been used in the past. For example, U.S. Pat. No. 4,163,028 involves the isomerization of xylenes and the conversion ethylbenzene conversion using a catalyst comprised of zeolite, typified by ZSM-5, and a hydrogenation metal such as platinum.

U.S. Pat. No. 4,899,011 involves a process in which a $C_8$ aromatic feed, which contains ethylbenzene and has been depleted in its para-xylene content, is contacted with a two catalyst system. The first catalyst dealkylates the ethylbenzene to benzene and ethane, while the second catalyst isomerizes the xylenes to increase the para-xylene content to a value at or approaching the thermal equilibrium value. The volume of the first catalyst is no greater than one-half of the catalyst bed volume and, most preferably, not greater than one-third of the volume of the catalyst bed.

U.S. Pat. No. 5,516,956 involves a process in which a $C_8$ aromatic feed, which has been depleted in its para-xylene content, is contacted with a two catalyst system. The catalyst used primarily to convert ethylbenzene comprises a zeolite that is selectivated with a selectivating agent containing silicon to improve its ethylbenzene conversion selectivity.

U.S. Pat. No. 6,008,425 involves a process for aromatics isomerization. The patent discloses a two catalyst system for the isomerization of xylenes and the conversion of ethylbenzene. The catalyst used primarily to convert ethylbenzene comprises zeolite bound by zeolite.

U.S. Pat. No. 6,576,581 involves a process for aromatics isomerization using a two component catalyst system. The catalyst used primarily to convert ethylbenzene comprises a non-zeolitic molecular sieve.

There is a need in the art to provide an improved process, which affords a high value product slate for ethylbenzene conversion and xylene isomerization.

SUMMARY OF THE INVENTION

The present invention is directed to a process for isomerizing xylenes present in a feed containing ethylbenzene. The process is carried out by contacting the feed under conversion conditions with a catalyst system comprising two catalysts. The first catalyst is unselectivated and comprises: (a) an intermediate pore size zeolite; (b) a hydrogenation component to deethylate ethylbenzene; and (c) an amorphous binder, said first catalyst requiring at least 50 minutes to sorb 30% of the equilibrium capacity of ortho-xylene at 120° C. and at an ortho-xylene partial pressure of 4.5±0.8 mm of mercury. The second catalyst comprises an intermediate pore size zeolite and requires less than 50 minutes to sorb 30% of the equilibrium capacity of ortho-xylene at 120° C. and at an ortho-xylene partial pressure of 4.5±0.8 mm of mercury. The amount of first catalyst present in the catalyst system is an volume greater than 55 percent based on the sum of the volumes of the first catalyst and second catalyst.

In a preferred embodiment, there is provided a process for upgrading a non-equilibrium feed mixture containing ethylbenzene and at least one xylene isomer with a catalyst system comprising two catalysts. The process comprises: (i) contacting said feed mixture under ethylbenzene conversion conditions with a first catalyst effective under said ethylbenzene conversion conditions to deethylate ethylbenzene in said feed mixture and produce an ethylbenzene-depleted product, wherein said first catalyst consists essentially of: (a) ZSM-5; (b) a hydrogenation component to deethylate ethylbenzene; and, (c) an amorphous binder, said first catalyst requiring at least 50 minutes to sorb 30% of the equilibrium capacity of ortho-xylene at 120° C. and at an ortho-xylene partial pressure of 4.5±0.8 mm of mercury; and (ii) contacting the ethylbenzene-depleted product under xylene isomerization conditions with a second catalyst comprising an ZSM-5, wherein said second catalyst less than 50 minutes to sorb 30% of the equilibrium capacity of ortho-xylene at 120° C. and at an ortho-xylene partial pressure of 4.5±0.8 mm of mercury. The amount of first catalyst present in the catalyst system is a volume greater than 55 percent based on the sum of the volumes of the first catalyst and second catalyst.

Preferably, the practice of the present invention results in exhaustively converting ethylbenzene and non-aromatics in the mixed ethylbenzene/xylene-containing feeds. The expression "exhaustively converting" means that per pass, at least fifty percent of the ethylbenzene is deethylated and at least thirty percent of the non-aromatic hydrocarbons, i.e., naphthenes and paraffins, are hydrocracked.

DETAILED DESCRIPTION OF THE INVENTION

Feedstock

In general, any aromatic $C_8$ mixture containing ethylbenzene and xylene may be used as feed to the process of this invention. Generally, such mixture will typically have an ethylbenzene content in the approximate range of 5 to 60 weight percent, an ortho-xylene content in the approximate range of 0 to 35 weight percent, a meta-xylene content in the approximate range of 20 to 95 weight percent and a para-xylene content in the approximate range of 0 to 15 weight percent. The feed, in addition to the above aromatic $C_8$ mixture, may contain non-aromatic hydrocarbons, i.e., naphthenes and paraffins, in an amount up to 30 weight percent. In a preferred embodiment, the invention provides means to process a mixture of $C_8$ aromatics such as that derived from catalytic reforming of a petroleum naphtha to a mixture of reduced ethylbenzene content and increased content of para-xylene. The invention is particularly effective in treating a para-xylene lean mixture of $C_8$ aromatics to increase the para-xylene concentration up to approximately the thermal equilibrium level.

The process of the present invention is especially suitable for the isomerization of $C_8$ aromatics streams that contain about 5 to about 60 wt. % ethylbenzene, e.g., about 25 to about 60 wt. % ethylbenzene. This range spans the range of ethylbenzene concentrations of streams that are derived from a reformer and a pyrolysis gasoline unit. The catalyst system can have high activity for cracking of normal and branched paraffins of the type present in unextracted $C_8$ aromatics streams.

Process Conditions

The conditions employed in the process are not narrowly defined, but generally include a temperature of from about 315 to about 537° C. (600 to 1000° F.), a pressure of from about 0 to about 500 psig (100 to 3550 kPa), a weight hourly space velocity (WHSV) of between about 0.01 and about 200 $hr^{-1}$, and a hydrogen, $H_2$, to hydrocarbon, HC, molar ratio of between about 0.05 and about 10. Preferably, these conditions include a temperature of from about 400 to about 482° C. (750 to 900° F.), a pressure of from about 50 to about 400 psig (445 to 2870 kPa), a WHSV of between about 3 and about 50 $hr^{-1}$, and a $H_2$ to HC molar ratio of between about 1 and about 5. The WHSV is based on the weight of catalyst composition, i.e., the total weight of active catalyst and, if used, binder therefor. For some applications, it is preferable that the process be run at a temperature from about 371 to about 400° C. (700 to 750° F.).

The catalyst system used in accordance with the present invention is multifunctional. One function of the catalyst system is to effect isomerization of the xylene components to a concentration approximately equal to thermal equilibrium, while another function of the catalyst system is to deethylate ethylbenzene (and to crack paraffins) with minimal xylene loss.

To effect high levels of conversion of ethylbenzene, while bringing the xylene components of the $C_8$ aromatics feed to thermal equilibrium in the isomerizer without excessive loss of xylenes to heavier aromatics and other components, the feed is contacted with the catalyst system, preferably under the conversion conditions described above. The conversion process described herein may be carried out as a batch type, semi-continuous or continuous operation. After use in a moving or fluidized bed reactor, the catalyst can be regenerated, in a regeneration zone in which the coke is burned from the catalyst in an oxygen containing atmosphere, e.g., air, at an elevated temperature after which the regenerated catalyst is recycled to the conversion zone for further contact with the charge stock. In a fixed bed reactor, regeneration can be carried out in a conventional manner by using initially an inert gas containing a small amount of oxygen (0.5 to 2 volume percent) to burn coke in a controlled manner so as to limit the temperature to a maximum of around about 450° C. to about 500° C.

In general, the xylene isomerization reaction is carried out in a fixed bed reactor containing the catalyst system. In a preferred embodiment, the two catalysts of the catalyst system are in sequential beds. That is, the catalyst of the catalyst system used in the process of the invention, which is effective for ethylbenzene conversion, forms a first bed, while the other catalyst of the catalyst system, which is effective for xylene isomerization, forms a second bed. Thus, the conversion process of the invention could be carried out in two different reactors, even at different process conditions. However, preferably, the feed is cascaded over the catalyst system disposed in sequential beds. In cascading, the feed is contacted with the two catalysts of the catalyst system without intervening separation of light gases.

The first catalyst, which is effective to deethylate ethylbenzene, is present in an amount greater than 55 percent by volume based on the sum of the volumes of the first catalyst and second catalyst of the catalyst system. Preferably, the first catalyst is employed in an amount that is greater than about 60 percent by volume. More preferably, the first catalyst is employed in an amount of at least about 75 percent of the volume based on the sum of the volumes of the first catalyst and second catalyst. Usually, the first catalyst will not employed in amounts greater than about 90 percent of the volume based on the sum of the volumes of the first catalyst and second catalyst.

After the conversion process, the isomerization product can be treated to isolate para-xylene and/or other desirable xylene(s). Thus, for example, the isomerizate product can be fed to a variety of para-xylene recovery units, such as a crystalizer, a membrane separation unit, or a selective adsorption unit, and thus the para-xylene may be isolated and recovered. The residual isomerizate can be stripped of products lighter than $C_8$ aromatics. Products heavier than $C_8$ aromatics in the residual isomerizate can be further processed or may be fractionated out. $C_8$ aromatics fractions from which para-xylene has been removed can be recycled to the isomerizer.

One result of the process of this invention is to convert the mixed xylene components of the feed containing para-xylene in an amount less than that at thermal equilibrium to an extent such that product from the isomerizer contains para-xylene in an amount at least approaching that of para-xylene in the xylene mixture produced at thermal equilibrium. Another result of the process of this invention is exhaustive conversion of ethylbenzene, i.e., at least 50 percent conversion in the feed which is converted.

Catalyst System

The catalyst system comprises two catalysts. The catalyst primarily effective to deethylate ethylbenzene, is unselectivated and will comprise an intermediate pore size zeolite, an amorphous binder, and an effective amount of a hydrogenation component to deethylate ethylbenzene.

The catalyst primarily effective for xylenes isomerization will comprise an intermediate pore size zeolite, preferably, a hydrogenation component, and, preferably, a binder.

Intermediate pore size zeolites have a pore size from about 5 to about 7 Å. Examples of suitable intermediate pore size zeolites for used in the present invention include ZSM-5, ZSM-11; ZSM-12; ZSM-21; ZSM-22; ZSM-23; ZSM-35; ZSM-38, ZSM-57; and ZSM-58. The preferred zeolite is ZSM-5.

Generally, the intermediate pore size zeolite, either directly or via initial ammonium exchange followed by calcination, is preferably hydrogen exchanged such that a predominant proportion of its exchangeable cations are hydrogen ions. In general, it is contemplated that more than 50 percent and preferably more than 75 percent of the cationic sites of the crystalline intermediate pore size zeolite will be occupied by hydrogen ions.

Original ions, e.g., alkali or alkaline earth metal, of the as-synthesized zeolite can be replaced in accordance with techniques well known in the art, at least in part, by ion exchange with other ions. Typical ion exchange techniques would be to contact the synthetic zeolite with a solution containing a salt of the desired replacing ion or ions. Examples of such salts include the halides, e.g., chlorides, nitrates and sulfates. Representative ion exchange techniques are disclosed in a wide variety of patents including U.S. Pat. Nos. 3,140,249; 3,140,251; and 3,140,253, each incorporated by reference herein.

Examples of hydrogenation components for use in the catalyst system include the oxide, hydroxide, sulfide, or free metal (i.e., zero valent) forms of Group VIII metals (i.e., Pt, Pd, Ir, Rh, Os, Ru, Ni, Co and Fe), Group IVA metals (i.e., Sn and Pb), Group VA metals (i.e., Sb and Bi), and Group VIIB metals (i.e., Mn, Tc and Re). Noble metals (i.e., Pt, Pd, Ir, Rh, Os and Ru) are preferred hydrogenation/dehydrogenation components. Combinations of catalytic forms of such noble or non-noble metal, such as combinations of Pt with Sn, may be used. The valence state of the metal is preferably in a reduced valence state, e.g., when this component is in the form of an oxide or hydroxide. The reduced valence state of this metal may be attained, in situ, during the course of a reaction, when a reducing agent, such as hydrogen, is included in the feed to the reaction.

The hydrogenation/dehydrogenation component may be incorporated into the catalyst by methods known in the art, such as ion exchange, impregnation or physical admixture. The metal containing salt is preferably water soluble. Examples of such salts include chloroplatinic acid, tetrammineplatinum complexes, platinum chloride, tin sulfate and tin chloride. The metal may be incorporated in the form of a cationic, anionic or neutral complex such as $Pt(NH_3)_4^{2+}$ and cationic complexes of this type will be found convenient for exchanging metals onto the zeolite. For example, a platinum modified catalyst can be prepared by first adding the catalyst to a solution of ammonium nitrate in order to convert the catalyst to the ammonium form. The catalyst is subsequently contacted with an aqueous solution of tetraamine platinum(II) nitrate or tetraamine platinum(II) chloride. Incorporation can be carried out in accordance with U.S. Pat. No. 4,312,790, which is hereby incorporated by reference. After incorporation of the metal, the catalyst can then be filtered, washed with water and calcined at temperatures of from about 250° C. to about 500° C.

The amount of hydrogenation/dehydrogenation component may be that amount which imparts or increases the catalytic ability of the overall catalyst to catalytically hydrogenate or dehydrogenate an organic compound under sufficient hydrogenation or dehydrogenation conditions. This amount is referred to herein as a catalytic amount. The amount of the hydrogenation-dehydrogenation component is suitably from about 0.001 to about 10 percent by weight, e.g., from about 0.1 to about 5 percent by weight, e.g., from about 0.1 to about 2 percent by weight, although this will, of course, vary with the nature of the component, less of the highly active noble metals, particularly platinum, being required than of the less active base metals.

The first catalyst will include an amorphous binder. Examples of such binder materials include clays, alumina, silica, silica-alumina, silica-magnesia, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia.

The second catalyst will preferably include a binder. Examples of such binders include the binders listed above for the first catalyst.

The relative proportions of intermediate pore size zeolite and binder may vary widely with the zeolite content ranging from between about 1 to about 99 percent by weight and more usually in the range of about 10 to about 80 percent by weight of the dry composite.

The form and the particle size of the catalyst are not critical to the present invention and may vary depending, for example, on the type of reaction system employed. Non-limiting examples of the shapes of the catalyst which may be independently employed for either or both of the catalysts in the present invention include balls, pebbles, spheres, extrudates, channeled monoliths, honeycombed monoliths, microspheres, pellets or structural shapes, such as lobes, pills, cakes, honeycombs, powders, granules, and the like, formed using conventional methods, such as extrusion or spray drying. Where, for example, the final particles are designed for use as a fixed bed, the particles may preferably be formed into particles having a minimum dimension of at least about 0.01 inch and a maximum dimension of up to about one-half inch or one inch or more. Spherical particles having a diameter of about 0.03 inch to about 0.25 inch, preferably about 0.03 inch to about 0.15 inch, are often useful, especially in fixed bed or moving bed operations. With regard to fluidized bed systems, it is preferred that the major amount by weight of the particles have a diameter in the range of about 10 microns to about 250 microns, more preferably about 20 microns to about 150 microns.

Each of the catalysts of the catalyst system will exhibit mutually exclusive xylene diffusional properties. These properties can be identified by noting the time (in minutes) required to sorb 30% of the equilibrium capacity of ortho-xylene at 120° C. and at an ortho-xylene partial pressure of 4.5±0.8 mm of mercury. This test is described in U.S. Pat. Nos. 4,117,026; 4,159,282; and Re. 31,782, which are hereby incorporated by reference. Herein, the equilibrium capacity of ortho-xylene is defined as greater than 1 gram of xylene(s) per 100 grams of zeolite. In accordance with the invention, the catalyst effective for ethylbenzene conversion will have a value (in minutes) in excess of about 50 and preferably greater than about 100, but less than 10,000 minutes, while on the other hand, the isomerization catalyst will require ortho-xylene sorption times of less than about 50 minutes and preferably less than about 10 minutes.

The alpha value of the intermediate pore size zeolite of the first catalyst, which is effective to convert ethylbenzene, will typically be at least about 100. Generally, the alpha value of the first catalyst will be in the range from about 100 to about 500, and preferably, it ranges from about 100 to about 300. The xylene diffusion properties of this catalysts are such that, under the process conditions described above, deethylation is favored over isomerization. The "alpha value" of a catalyst reflects the relative activity of the catalyst with respect to a high activity silica-alumina cracking catalyst. The alpha value test is described in U.S. Pat. No. 3,354,078; in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

When the intermediate pore size zeolite of the first catalyst is ZSM-5, the requisite diffusion properties are satisfied by providing ZSM-5 in crystals, the minimum dimension of which is at least 1μ (one micron). Production of ZSM-5 with a crystal size, the minimum dimension of which is at least 1μ is described in, for example, U.S. Pat. No. 4,375,458, which is hereby incorporated by reference The second catalyst of the catalyst system is effective to isomerize the xylenes of the feed containing $C_8$ aromatics. This catalyst can comprise ZSM-5. The acidity of this catalyst, e.g., ZSM-5, expressed as the alpha value, will preferably be less than 100. Preferably, the ZSM-5 will have an alpha value of at most 50; and preferably, the alpha value will range from 5 to 25. The minimum dimension of crystals of ZSM-5 used in this catalyst will usually be less than 1μ, as determined by electron microscopy, and generally less than 0.5μ. Preferably, that minimum dimension of ZSM-5 is at most 0.10μ; and most preferably that minimum dimension will range from about 0.02 to 0.05μ.

The following examples illustrate the invention.

EXAMPLE I

I. Preparation of Ethylbenzene Conversion Catalyst

A 1/16" quadrulobe shaped, first catalyst was prepared by extruding 65 parts by weight of ZSM-5 having a crystal size of about 1 micron with 35 parts by weight of alumina (on a dry basis). The extrudate was then dried, calcined in a nitrogen atmosphere, exchanged with ammonium nitrate, then calcined in air at 538° C. Next, an amount of 0.5 weight percent of rhenium was then added to this catalyst, via incipient wetness impregnation. This catalyst was then calcined in air at 538° C. to give the first catalyst of the catalyst system.

II. Preparation of Xylenes Isomerization Catalyst

A 1/16" cylindrically shaped, second catalyst was prepared by extruding 65 parts by weight of ZSM-5 having a crystal size of about 0.02 to 0.05 micron with 35 parts of alumina (on a dry basis). The extrudate was then dried, calcined in a nitrogen atmosphere, exchanged with ammonium nitrate, then calcined in air at 538° C. Next, an amount of 0.5 weight percent of rhenium was then added to this catalyst, via incipient wetness impregnation. This catalyst was then calcined in air at 538° C. to give the second catalyst of the catalyst system.

EXAMPLE II

The conversion of ethylbenzene and xylene isomerization was evaluated using a catalyst containing varying amounts of first and second catalysts.

The evaluations were conducted in automated units with on-line GC sampling. The catalyst system was loaded into a 3/8" diameter, stainless steel tube reactor (with sand as inert packing material). The catalyst systems were stacked by loading various amounts of first catalyst (top bed) and second catalyst (bottom bed). For example, a catalyst system containing 50 percent by volume of first catalyst and 50 percent by volume of second catalyst, was placed into the reactor by placing 0.5 g of first catalyst over 0.5 g of second catalyst. After loading, the catalyst systems were heated in a nitrogen atmosphere to 350° C. and reduced in hydrogen at this temperature for 1 hour. The reactor was then heated to reaction temperature, and feed was introduced. The feed was alumina-percolated.

The Table shows a comparison of the performance of the process using a catalyst system containing varying amounts of top bed first catalyst and bottom bed second catalyst.

The feed used in the tests along with the conditions and results of the tests are shown below in the Table. The results were obtained after the feed had been on stream from 2 to 4 days.

TABLE

| | | Column Number | | | | |
|---|---|---|---|---|---|---|
| | | A | B | C | D | E |
| Top Bed | Feed | 100% | 75% | 50% | 25% | 0% |
| Bottom Bed | | 0% | 25% | 50% | 75% | 100% |
| Conditions | | | | | | |
| Temperature (° F.) | | 710.5 | 719.4 | 739.0 | 769.7 | 820.3 |
| Pressure (psig) | | 367.1 | 348.0 | 371.4 | 376.1 | 362.9 |
| WHSV (1/Hr) | | 10.0 | 10.0 | 10.0 | 10.0 | 10.0 |
| $H_2$/HC (molar) | | 1.5 | 1.5 | 1.5 | 1.5 | 1.5 |
| GC Analysis (Wt. %) | | | | | | |
| $C_{5-}$ | | 1.72 | 1.88 | 2.08 | 2.00 | 2.36 |
| Total Saturates | 0.00 | 0.07 | 0.07 | 0.09 | 0.09 | 0.00 |
| Benzene | | 5.28 | 5.60 | 5.87 | 5.61 | 5.70 |
| Toluene | 1.00 | 2.19 | 2.24 | 2.44 | 2.45 | 2.64 |
| Ethylbenzene | 14.80 | 5.66 | 5.53 | 4.98 | 5.23 | 5.25 |
| Para-xylene | 10.70 | 20.13 | 20.10 | 19.95 | 19.87 | 19.38 |
| Meta-xylene | 62.39 | 45.32 | 44.78 | 44.47 | 43.84 | 42.70 |
| Ortho-xylene | 11.11 | 18.55 | 18.78 | 18.94 | 19.30 | 19.23 |
| Total $C_{9+}$ | 0.00 | 1.08 | 1.03 | 1.16 | 1.55 | 2.66 |
| EB Conversion | | 61.7% | 62.6% | 66.3% | 64.7% | 64.5% |
| Xylene Loss | | 0.2% | 0.7% | 1.0% | 1.4% | 3.4% |
| Para-xylene/ Total Xylenes | 12.71% | 24.0% | 24.0% | 23.9% | 23.9% | 23.8% |
| Para-xylene Approach To Equilibrium | | 103.2% | 104.0% | 103.5% | 104.2% | 104.2% |

The results of the tests show that the xylenes isomerization/ethylbenzene dealkylation process of the present invention had advantages over a xylenes isomerization/ethylbenzene dealkylation process using a catalyst system containing 50% or less by volume of first catalyst. The advantages include the following:

more para-xylene production less heavy materials ($C_9$+)

lower xylene loss operation at lower temperature

The higher para-xylene yield, lower xylene loss, and lower $C_9$+ yield using the process of the present invention results in a higher value product. The lower temperatures for the process of the present invention, e.g., process using a catalyst system containing at least 55 percent by volume of first catalyst, is also beneficial, because of longer catalyst cycle times and may be used in reactors that are limited by the necessity to operate at lower temperatures.

What is claimed is:

1. A process for isomerizing xylenes present in a feed containing ethylbenzene comprising:

contacting said feed under conversion conditions with a catalyst system containing a first catalyst and a second catalyst, said first catalyst being unselectivated and comprising: (a) an intermediate pore size zeolite; (b) Re to deethylate ethylbenzene; and (c) an amorphous binder, said first catalyst requiring at least 50 minutes to sorb 30% of the equilibrium capacity of ortho-xylene at 120° C. and at an ortho-xylene partial pressure 4.5±0.8 mm of mercury; and said second catalyst comprises an intermediate pore size zeolite and requires less than 50 minutes to sorb 30% of the equilibrium capacity of ortho-xylene at 120° C. and at an ortho-xylene partial pressure of 4.5±0.8 mm of mercury;

wherein the amount of said first catalyst present in said catalyst system is an amount greater than 55 percent and by volume based on the sum of the volumes of the first catalyst and second catalyst.

2. The process recited in claim 1, wherein the amount of said first catalyst present in said catalyst system is an amount greater than 60 percent by volume based on the sum of the volumes of the first catalyst and second catalyst.

3. The process recited in claim 1, wherein the amount of said first catalyst present in said catalyst system is an amount of at least 75 percent by volume based on the sum of the volumes of the first catalyst and second catalyst.

4. The process recited in claim 1, wherein the conversion conditions include a temperature from about 315 to about 5370C., a pressure of from about 0 to about 500 psig, a weight hourly space velocity of between about 0.01 and about 200 hr$^{-1}$, and a hydrogen to hydrocarbon molar ratio of between about 0.05 and about 10.

5. The process recited in claim 1, wherein said feed has an ethylbenzene content in the range of from about 5 to about 60 weight percent, an ortho-xylene content in the range of from 0 to about 35 weight percent, a meta-xylene content in the range of from about 20 to about 95 weight percent and a paraxylene content in the range of from 0 to about 15 weight percent.

6. The process recited in claim 1, wherein said feed has an ethylbenzene content from about 25 to about 60 wt. %.

7. The process recited in claim 1, wherein said intermediate pore size zeolite of said first catalyst and second catalyst is selected from the group consisting of ZSM-5, ZSM-11; ZSM-12; ZSM-21; ZSM-22; ZSM-23; ZSM-35; ZSM-38, ZSM-57; and ZSM-58.

8. The process recited in claim 1, wherein said intermediate pore size zeolite present in said first catalyst and said second catalyst is ZSM-5.

9. The process recited in claim 8, wherein said intermediate pore size zeolite present in said first catalyst has an alpha value from about 100 to about 300.

10. The process recited in claim 8, wherein said intermediate pore size zeolite present in said second catalyst has an alpha value of less than about 100.

11. The process recited in claim 9, wherein the crystals of said intermediate pore size zeolite present in said first catalyst have a crystal size of at least about 1µ.

12. The process recited in claim 10, wherein the crystals of said intermediate pore size zeolite present in said second catalyst have a crystal size of less about 1µ.

13. The process recited in claim 8, wherein said amorphous binder of said first catalyst is alumina or silica.

14. The process recited in claim 1, wherein at least 30 percent of the ethylbenzene present of the feed is converted to benzene.

15. The process recited in claim 1, wherein the feed is contacted with the first catalyst before the feed is contacted with the second catalyst.

16. The process recited in claim 1, wherein the process is carried out in a fixed bed reactor.

17. The process recited in claim 1, wherein the first catalyst and the second catalyst are in sequential beds.

18. The process recited in claim 1, wherein the second catalyst further comprises at least one hydrogenation catalyst.

19. The process recited in claim 18, wherein said at least one hydrogenation component of second catalyst is a Group VII metal or a Group VIIB metal.

20. The process recited in claim 18, wherein the at least one hydrogenation component of the second catalyst is platinum, rhenium, or mixtures thereof.

21. The process recited in claim 6, wherein said feed contains up to 30 weight percent of non-aromatics and at least 30 percent of the non-aromatics are hydrocracked.

22. The process recited in claim 1, wherein said feed is cascaded over the catalyst system.

23. The process recited in claim 4, wherein said temperature is in the range of from about 371 to about 400° C.

24. A process for upgrading a non-equilibrium feed mixture containing ethylbenzene and at least one xylene isomer with a catalyst system comprising a first catalyst and a second catalyst, said process comprising:

(i) contacting said feed mixture under ethylbenzene conversion conditions with a first catalyst effective under said ethylbenzene conversion conditions to deethylate ethylbenzene in said feed mixture and produce an ethylbenzene-depleted product, wherein said first catalyst consists essentially of : (a) ZSM-5 having an alpha value from about 100 to about 300 and a crystal size of at least 1µ; (b) Re, and mixtures and, (c) a binder selected from the group consisting of silica, alumina, and mixtures thereof; said first catalyst requiring at least 50 minutes to sorb 30% of the equilibrium capacity or ortho-xylene at 120 ° C. and at an ortho-xylene partial pressure of 4.5±0.8 mm of mercury; and, (ii) contacting the ethylbenzene-depleted product under xylene isomerization conditions with a second catalyst comprising (a) ZSM-5 having an alpha value less than about 100 and a crystal size no greater than 0.10µ; (b) a hydrogenation component; and (c) a binder comprising silica, alumina, or mixtures thereof, said second catalyst requiring less than 50 minutes to sorb 30% of the equilibrium capacity of ortho-xylene at 120 ° C. and at an ortho-xylene partial pressure of 4.5±0.8 mm of mercury; wherein the amount of said first catalyst present in said catalyst system is an amount greater than 55 percent by volume based on the sum of the volumes of the first catalyst and second catalyst.

25. The process recited in claim 24, wherein the amount of said first catalyst present in said catalyst system is an amount greater than 60 percent by volume based on the sum of the volumes of the first catalyst and second catalyst.

26. The process recited in claim 24, wherein the amount of said first catalyst present in said catalyst system is an amount of at least 75 percent by volume based on the sum of the volumes of the first catalyst and second catalyst.

27. The process recited in claim 24, wherein the conversion conditions include a temperature from about 315 to about 537° C., a pressure of from about 0 to about 500 psig, a weight hourly space velocity of between about 0.01 and about 200 hr$^{-1}$, and a hydrogen to hydrocarbon molar ratio of between about 0.05 and about 10.

28. The process recited in claim 24, wherein said feed has an ethylbenzene content in the range of from about 5 to about 60 weight percent, an ortho-xylene content in the range of from 0 to about 35 weight percent, a meta-xylene content in the range of from about 20 to about 95 weight percent and a paraxylene in the range of from 0 to about 15 weight percent.

29. The process recited in claim 28, wherein said feed has an ethylbenzene content from about 25 to about 60 wt. %.

30. The process recited in claim 24, wherein said hydrogenation component of said second catalyst is Pt or Re.

31. The process recited in claim 24, wherein at least 30 percent of the ethylbenzene present of the feed is converted to benzene.

32. The process recited in claim 24, wherein the process is carried out in a fixed bed reactor.

33. The process recited in claim 24, wherein the first catalyst and the second catalyst are in sequential beds.

34. The process recited in claim 24, wherein said feed contains up to 30 weight percent of non-aromatics and at least 30 percent of the non-aromatics are hydrocracked.

35. The process recited in claim 24, wherein said feed is cascaded over the catalyst system.

36. The process recited in claim 27, wherein said temperature is in the range of from about 371 to about 400° C.

* * * * *